United States Patent
Tzao et al.

(10) Patent No.: US 9,192,299 B2
(45) Date of Patent: Nov. 24, 2015

(54) HEALTH CHECK PATH EVALUATION INDICATOR BUILDING SYSTEM, METHOD THEREOF, DEVICE THEREWITH, AND COMPUTER PROGRAM PRODUCT THEREIN

(71) Applicant: Industrial Technology Research Intitute, Hsinchu (TW)

(72) Inventors: Szu-Han Tzao, Taipei (TW); Jung-Ping Chen, New Taipei (TW); Yin-Pin Yang, Hsinchu County (TW); Yue-Min Jiang, New Taipei (TW); Yu-Chieh Pan, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 265 days.

(21) Appl. No.: 13/870,999

(22) Filed: Apr. 26, 2013

(65) Prior Publication Data
US 2014/0168246 A1  Jun. 19, 2014

(30) Foreign Application Priority Data
Dec. 19, 2012  (TW) .............................. 101148426 A

(51) Int. Cl.
*A61B 5/00* (2006.01)
*G06F 19/00* (2011.01)

(52) U.S. Cl.
CPC .. *A61B 5/00* (2013.01); *G06F 19/30* (2013.01)

(58) Field of Classification Search
CPC ......... G06F 19/00; G06F 19/24; G06F 19/26; G06F 19/28; G06F 19/30; G06F 19/32; G06F 19/322; G06F 19/3487
See application file for complete search history.

(56) References Cited

U.S. PATENT DOCUMENTS 6,909,981 B2   6/2005  Gavin et al.
8,679,009 B2 *  3/2014  Osorio .......................... 600/300
(Continued)

FOREIGN PATENT DOCUMENTS

CN   101504693   8/2009
TW   I278768    4/2007
(Continued)

OTHER PUBLICATIONS

Tony Hsiu-Hsi Chen, et al., "Community-Based Multiple Screening Model: Design, Implementation, and Analysis of 42,387 Participants Taiwan Community-Based Integrated Screening Group", Cancer, Community-Based Integrated Screening, vol. 100, No. 8, Mar. 3, 2004, pp. 1734-1743.
(Continued)

Primary Examiner — Antonio A Caschera
(74) Attorney, Agent, or Firm — Jianq Chyun IP Office

(57) ABSTRACT

A health check evaluation indicator building method includes the following steps. A visualization process is performed to produce source graphic data on a plurality of features and attributes according to a time series, wherein each of the source graphic data includes a group number. Then, a similarity comparison is performed between the source graphic data and a plurality of target graphic data with the same group number to produce a plurality of similarity scores, where the minimum thereof corresponds to role model graphic data. Based on the role model graphic data, one of a best proposal and an alternative proposal is selected and a result thereof is fed back after execution. A health check evaluation indicator building system and a computer readable medium to embody the above method are also disclosed.

13 Claims, 5 Drawing Sheets

(56) References Cited

U.S. PATENT DOCUMENTS

| | | | |
|---|---|---|---|
| 2007/0027368 A1* | 2/2007 | Collins et al. | 600/300 |
| 2011/0077958 A1 | 3/2011 | Breitenstein et al. | |
| 2011/0129131 A1* | 6/2011 | Avinash et al. | 382/128 |

FOREIGN PATENT DOCUMENTS

| | | |
|---|---|---|
| TW | 200832237 | 8/2008 |
| TW | I313168 | 8/2009 |
| TW | 201020960 | 6/2010 |
| TW | 201035902 | 10/2010 |
| TW | 201118632 | 6/2011 |

OTHER PUBLICATIONS

Jiayu Zhou, et al., "Modeling Disease Progression via Fused Sparse Group Lasso", ACM, KDD'12, Proceedings of the 18th ACM SIGKDD international conference on Knowledge discovery and data mining, Aug. 12-16, 2012, pp. 1095-1103.

Parikshit Sondhi, et al., "SympGraph: A Framework for Mining Clinical Notes through Symptom Relation Graphs", ACM, KDD'12, Proceedings of the 18th ACM SIGKDD international conference on Knowledge discovery and data mining, Aug. 12-16, 2012, pp. 1167-1175.

Guo-Cheng Lan, et al., "Analysis and forecasting system building health trends and disease relevance utilizing data-mining technique", SHMS 2002, Aug. 1, 2012, pp. 22-33.

Igor Kononenko, "Machine Learning for Medical Diagnosis: History, State of the Art and Perspective", Artificial Intelligence in Medicine, vol. 23, 2001, pp. 89-109.

"Office Action of Taiwan Counterpart Application", issued on Oct. 30, 2014, p. 1-p. 17.

* cited by examiner

410

VS

420

HEALTH CHECK PATH EVALUATION INDICATOR BUILDING SYSTEM, METHOD THEREOF, DEVICE THEREWITH, AND COMPUTER PROGRAM PRODUCT THEREIN

CROSS-REFERENCE TO RELATED APPLICATION

This application claims the priority benefit of Taiwan application serial no. 101148426, filed on Dec. 19, 2012. The entirety of the above-mentioned patent application is hereby incorporated by reference herein and made a part of this specification.

BACKGROUND

1. Technical Field

The disclosure relates to a health check path evaluation indicator building technique.

2. Related Art

A biomarker may be regarded as an objective clinical measurement or an evaluation parameter and may also be used for monitoring or predicting the development of normal physiological phenomenon or diseases. However, physiological changes are undetectable during intervals between annual health check, which is obviously inadequate for disease risk prevention. Especially, test values of the biomarker are dynamic values, and the obtained data may have a large difference according to different environments and different self-condition of a testee. Therefore, the obtained test data is relatively unstable compared to physical feature data. In order to obtain relatively stable test data, multiple samplings and sample testing are required.

A complete health check procedure includes many check items, and the test procedures thereof are expensive and time-consuming. Moreover, a health check process suitable for one individual may not satisfy different individuals. In consider of time and economic cost, willingness to intuitively participate to the health check is not high. On the other hand, the depth and penetration of check items of a general health check are inadequate. In terms of the items required to be further checked, the procedures thereof are merely treated as a formality or routine in consideration of the coverage range of such health check.

Therefore, it is important to provide a health check system capable of performing regular evaluation for different individuals.

SUMMARY

The disclosure is directed to a health check path evaluation indicator building method, which includes the following steps. First, a plurality of attributes are provided in a time series, wherein each of the attributes has a plurality of features. In the method, a visualization process is performed on the features and the attributes according to the time series to produce source graphic data, wherein the source graphic data has a group number. Then, a similarity comparison is performed between the source graphic data and a plurality of target graphic data with the same group number to produce a plurality of similarity scores, wherein the minimum value among the similarity scores corresponds to best role model graphic data. Based on the best role model graphic data, one of a best proposal and an alternative proposal is selected, wherein the best proposal and the alternative proposal respectively have a plurality of items. All of the items in the best proposal correspond to the best role model graphic data, and a part of the items in the alternative proposal corresponds to the best role model graphic data. A result is fed back after the best proposal or the alternative proposal is executed.

The disclosure is directed to a health check path evaluation indicator building system including a data providing unit, a data receiving unit, a visualization processing unit, a target graphic database, a similarity comparison unit, a best role model generator, an information sample database, a path development prediction module, and a feedback unit. The data providing unit provides a plurality of attributes in a time series, wherein each of the attributes has a plurality of features. The data receiving unit is used to receive the features and the attributes. The visualization processing unit performs a visualization process on the features and the attributes according to the time series to produce source graphic data, wherein the source graphic data has a group number. The target graphic database stores a plurality of target graphic data, wherein each of the target graphic data has a group number. The similarity comparison unit is coupled to the visualization processing unit and the target graphic database and is used for performing a similarity comparison between the source graphic data and the plurality of target graphic data with the same group number to produce a plurality of similarity scores. The best role model generator is coupled to the similarity comparison unit and selects best role model graphic data from the target graphic data, wherein the similarity score between the source graphic data and the best role model graphic data is the minimum value among the similarity scores. The information sample database is used to store a plurality of proposals. The path development prediction module is coupled to the best role model generator and the information sample database and selects one of a best proposal and an alternative proposal from the information sample database according to the best role model graphic data. wherein the best proposal and the alternative proposal respectively have a plurality of items. All of the items of the best proposal correspond to the best role model graphic data, and a part of the items of the alternative proposal corresponds to the best role model graphic data. The feedback unit is coupled to the target graphic database and feeds back a result to the target graphic database after the best proposal or the alternative proposal is executed.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION OF DISCLOSED EMBODIMENTS

A part of embodiments of the disclosure are described in detail below with reference of figures. These embodiments are only a part of the disclosure, and are not all of applicable embodiments of the disclosure. To be more specific, these embodiments are only examples for the device and method in the claims of the disclosure.

Figure 1:
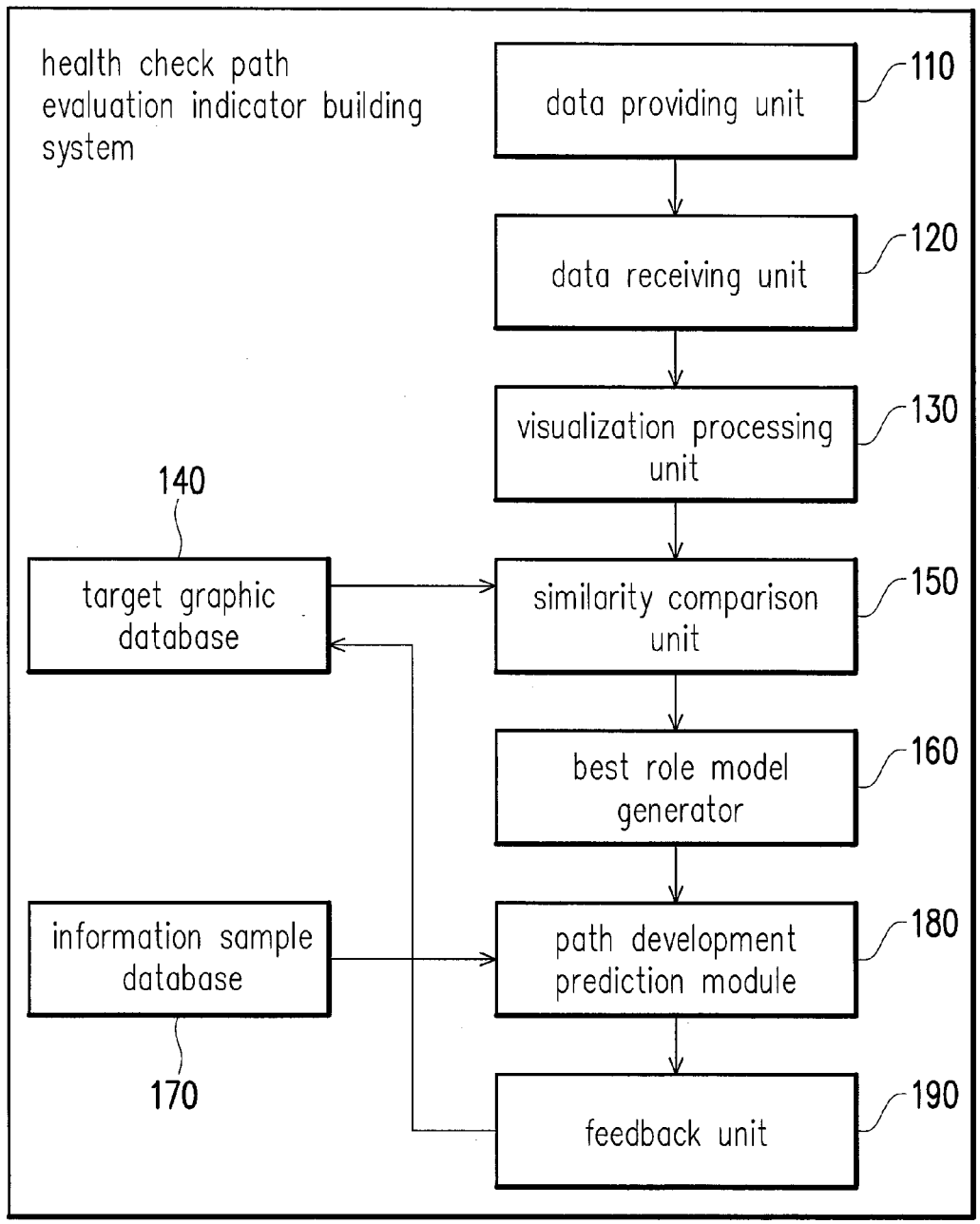
FIG. 1 is a block schematic diagram of a health check path evaluation indicator building system according to an embodiment of the disclosure.
Figure 2:
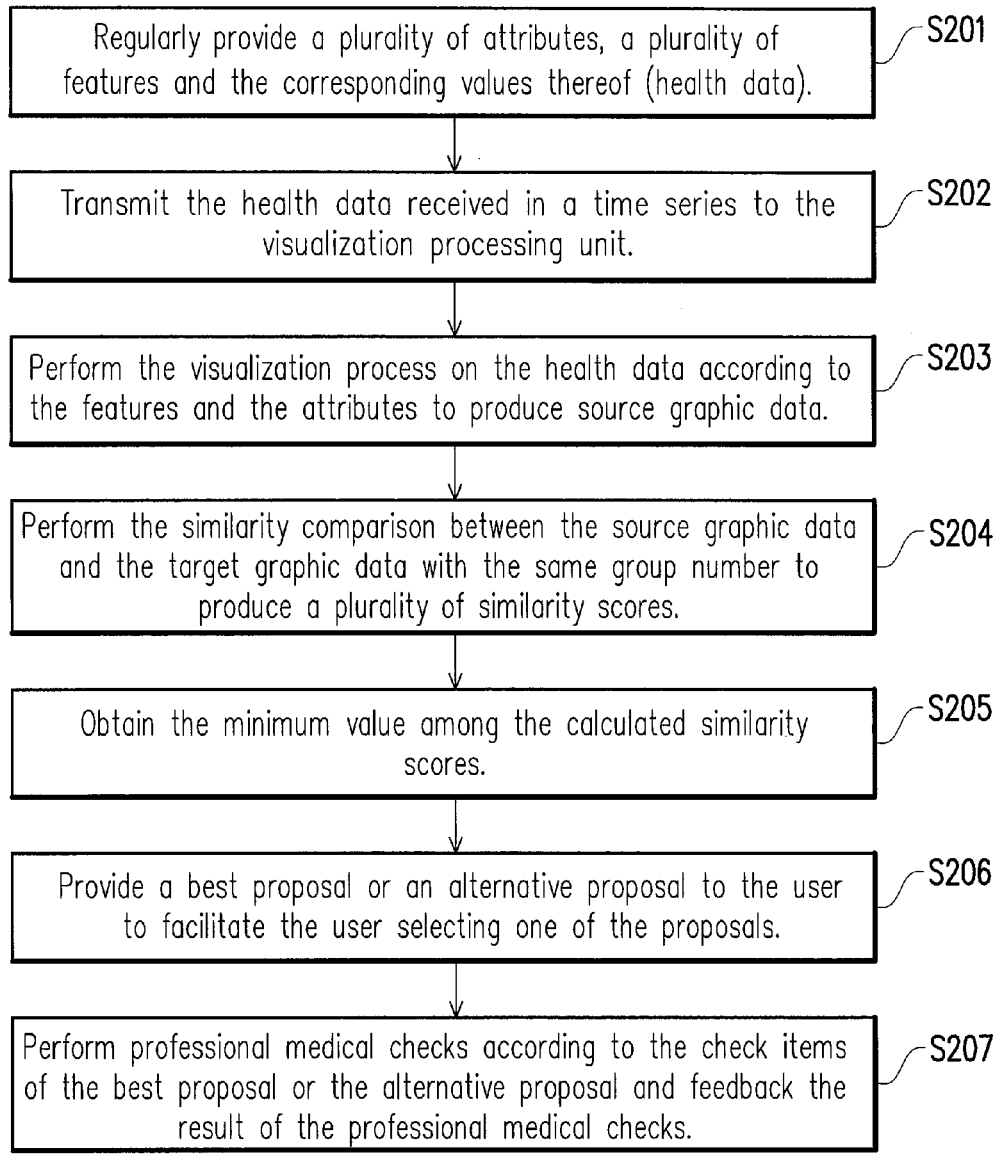
FIG. 2 is a flowchart of a health check path evaluation indicator building method according to an embodiment of the disclosure.

FIG. 1 is a block schematic diagram of a health check path evaluation indicator building system according to an embodiment of the disclosure, and FIG. 2 is a flowchart of a health check path evaluation indicator building method according to an embodiment of the disclosure. The embodiments are only used for descriptions and are not used to limit the disclosure.

Referring to FIG. 1, the health check path evaluation indicator building system 100 in the present embodiment includes a data providing unit 110, a data receiving unit 120, an visualization processing unit 130, a target graphic database 140, a similarity comparison unit 150, a best role model generator 160, an information sample database 170, a path development prediction module 180, and a feedback unit 190.

The aforementioned components are first introduced and the details thereof are disclosed with reference of the flowchart of the health check path evaluation indicator building method of FIG. 2. The data providing unit 110 provides a plurality of attributes in a time series, wherein each of the attributes has a plurality of features. In the present embodiment, the data providing unit 110 may be composed of a front-end self-evaluation module (not shown) and an physical examination assisting tool module (not shown), though the disclosure is not limited thereto. The data receiving unit 120 is used to receive the aforementioned features and the aforementioned attributes. The visualization processing unit 130 performs a visualization process on the features and the attributes according to the time series to produce source graphic data, wherein the source graphic data has a group number. The target graphic database 140 stores a plurality of target graphic data, wherein each of the target graphic data has a group number. The similarity comparison unit 150 is coupled to the visualization processing unit 130 and the target graphic database 140, and is used to perform a similarity comparison between the source graphic data and a plurality of the target graphic data with the same group number in the target graphic database 140 to produce a plurality of similarity scores. The best role model generator 160 is coupled to the similarity comparison unit 150 and selects best role model graphic data from the target graphic data with the same group number, wherein a similarity score between the best role model graphic data and the target graphic data is the minimum value among the similarity scores. The information sample database 170 is used to store a plurality of proposals. The path development prediction module 180 is coupled to the best role model generator 160 and the information sample database 170, and selects one of a best proposal and an alternative proposal from the information sample database 170 according to the best role model graphic data, wherein the best proposal and the alternative proposal respectively include a plurality of items. All of the items of the best proposal correspond to the best role model graphic data, and a part of the items of the alternative proposal corresponds to the best role model graphic data. The feedback unit 190 is coupled to the target graphic database 140, and feeds back a result to the target graphic database 140 after the best proposal or the alternative proposal is executed.

Referring to both FIG. 1 and FIG. 2, detail steps of the health check path evaluation indicator building method in FIG. 2 are described below with reference of the health check path evaluation indicator building system of FIG. 1.

In the present embodiment, the data providing unit 110 includes the front-end self-evaluation module and the physical examination assisting tool module. The front-end self-evaluation module regularly provides an online health questionnaire to obtain survey data from the user. The content of the online health questionnaire includes a plurality of attributes such as physiological parameters, demographic variables, disease symptoms, diet habits, exercise habits, medical history information. Each of the attributes includes a plurality of features, wherein the features may be a plurality of questions. For example, in an attribute of stroke, the user is asked whether to have features of numb hands and feet, headache, temporary vision loss, etc., and the user replies according to individual body symptoms. A reply of each feature may be converted into a numerical value. The front-end self-evaluation module transmits a result of the questionnaire to the physical examination assisting tool module, and the physical examination assisting tool module evaluates the result of the questionnaire.

If the evaluated result indicates that the user belongs to a high-risk group of a certain disease, a health check package suitable for the user is recommended according to the evaluated result so as to perform self-sampling at home. The health check package is, for example, a cardiovascular risk health check package, a metabolic risk health check package, a stroke risk health check package, or a breast cancer risk health check package. In order to improve feasibility, the above health check packages may be obtained from local clinics or pharmacies. After the user completes self-sampling, the user may send the self-samples to a designated biochemical experimental test center for tests so as to obtain tested data of the user. The tests may also include a plurality of attributes such as a blood test and a urine test. Similarly, each of the attributes may include a plurality of features. For example, the attribute of the blood test may include features of white blood cell, red blood cell, hemoglobin, hematocrit and platelet, etc. Each feature is also a numerical value, which is the aforementioned tested data. The data providing unit 110 regularly transmits the survey data and the tested data, i.e. the attributes, the features and the corresponding values thereof, to the data receiving unit 120 (step S201). For simplicity, the survey data and the tested data are jointly referred to as health data.

Then, the data receiving unit 120 transmits the health data received in a time series to the visualization processing unit 130 (step S202). Moreover, the data receiving unit 120 may assign a group number to the health data according to the health check package used by the user. The visualization processing unit 130 performs the visualization process on the health data according to the features and the attributes based on the time series to produce source graphic data (step S203). A method of the visualization process is, for example, to present the health data in a visualized form such as a thermodynamic chart or a contour map. In the present embodiment, the source graphic data is presented in a form of a thermodynamic chart, though the disclosure is not limited thereto.

Figure 3:
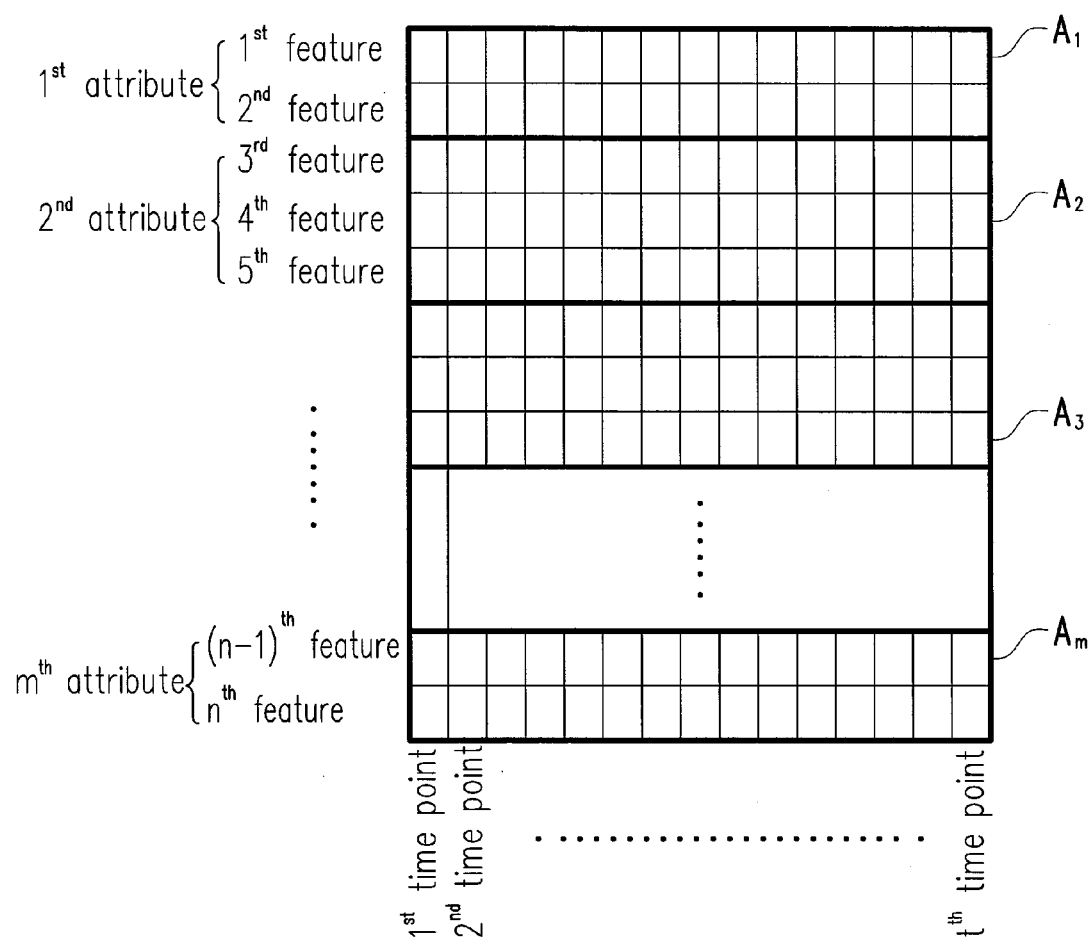
FIG. 3 illustrates an arranging method of each element in a source matrix A.

Regarding the visualization process of the thermodynamic chart, it is assumed that the user perform the health check in a time series with t periods. It is also assumed that the health data of the user has n features, and each feature corresponds to one of m attributes, and the health data is stored in a source matrix A according to the attributes. FIG. 3 illustrates an arranging method of each element in the source matrix A. Referring to FIG. 3, the source matrix A has n rows and t columns, and an element $a_{ij}$ of the source matrix A represents the health data with an i-th feature at a j-th time point, wherein i=0, 1, . . . , n and j=0, 1, . . . , t. The health data is arranged according to the attributes corresponding to the features, and the source matrix A formed by the n features within the t periods is divided into m feature group blocks $A_1, A_2, \ldots, A_m$, i.e. the features in each of the feature group blocks have the same attribute. Then, according to an interval range in which the value of each of the health data is, each of the health data is set to a different color so as to complete the visualization process to produce the source graphic data.

Regarding the visualization process of the contour map, a method of calculating the feature group blocks thereof is the same as that of the visualization process of the thermodynamic chart, though when the visualization is performed based on contour lines. According to an interval range in which the normalized/standardized value of each of the health data is, each of health data is set to a different contour line, and the health data within to the same interval may form a closed curve. An interior area enclosed by the contour line is treated as a comparison reference for other cases.

The health check path evaluation indicator building system 100 includes the target graphic database 140, which is used to store a plurality of target graphic data. Each of the target graphic data may be a thermodynamic chart of the health data of each of the other users, wherein the target graphic data may respectively have a group number according to the health check packages used by the users. For example, a first group may be the users with a stroke disease and the stroke risk health check package is used for self-sampling. A second group may be the users with a metabolic disease and the metabolic risk health check package is used. The target graphic database 140 may be dynamically updated to increase the quantity of the target graphic data.

Then, the visualization processing unit 130 transmits the source graphic data to the similarity comparison unit 150. Moreover, the similarity comparison unit 150 performs similarity comparison between the source graphic data and a plurality of target graphic data with the same group number in the target graphic database 140 to produce a plurality of similarity scores (step S204). In the present embodiment, the distance between the compared data is obtained by adapting the algorithm of the squared Euclidean distance for recognizing similarity difference, though the disclosure is not limited thereto. In other embodiments, the algorithm of the similarity score may also be multi-dimensional scaling of principal component analysis, multivariate statistical analysis or machine learning commonly used in computer image recognition.

For example, it is assumed that the source matrix A used for representing the source graphic data uses the cardiovascular risk health check package for self-sampling and the group number thereof is β. It is further assumed that target matrices $B^{(1)}, B^{(2)}, \ldots, B^{(p)}$ representing the target graphic data also use the cardiovascular risk health check package for self-sampling and the group number thereof is β, wherein p>1. Since the user represented by the source matrix A and the users represented by the target matrices $B^{(1)}, B^{(2)}, \ldots, B^{(p)}$ with the group value of β use the same health check package for the self-health check sampling, the target matrices $B^{(1)}, B^{(2)}, \ldots, B^{(p)}$ respectively have n rows, t columns and m feature group blocks. The arrangement of the target matrices is the same as that of the source matrix A, and an element $b_{ij}^{(k)}$ represents the health data with an i-th feature at a j-th time point in the target matrix $B^{(k)}$, wherein i=0, 1, . . . , n, j=0, 1, . . . , t, and k=0, 1, . . . , p. Then, the similarity comparison unit 150 calculates the similarity scores between the source matrix A and the target matrices $B^{(1)}, B^{(2)}, \ldots, B^{(p)}$, and transmits the similarity scores to the best role model generator 160. A method for calculating the similarity scores is, for example, to calculate the squared Euclidean distance between the source matrix A and the target matrices $B^{(1)}, B^{(2)}, \ldots, B^{(p)}$. Moreover, a weighting matrix W with different proportions allocated to the feature group blocks divided according to different attributes is used, wherein W is a diagonal matrix having n rows and n columns, and an element $w_{ij}$ represents the weight distributed to the feature group block (or attribute) corresponding to the i-th feature. The so-called weight is used for an indicator, and the weight of a certain indicator refers to a relative importance of the indicator in overall. For example, regarding the cardiovascular disease, weights allocated to features of blood pressure, blood glucose and blood lipid, etc. are higher than weights allocated to the other features. Accordingly, it is easier to distinguish the differences among the compared features due to the amplification effect of the weighting coefficients.

Then, the best role model generator 160 obtains the minimum value among the calculated similarity scores (step S205). Such minimum value is referred to as a minimum similarity score $S_{min}$ and is represented by the following mathematic equation:

$$S_{min} = \underset{\beta}{\operatorname{argmin}} \sum_{j=1}^{t} (a_j - b_j^{(k)})^T W (a_j - b_j^{(k)}),$$

wherein $a_j$ and $b_j^{(k)}$ are column vectors, i.e. $a_j$ and $b_j^{(k)}$ may be respectively represented as $a_j = [a_{1j} a_{2j} \ldots a_{nj}]^T$ and $b_j^{(k)} = [b_{1j}^{(k)} b_{2j}^{(k)} \ldots b_{ij}^{(k)}]^T$. The target graphic data corresponding to the minimum similarity score $S_{min}$ is the best role model graphic data, i.e. the health data of the source matrix A and that of the best role model graphic data have the minimum similarity score.

It should be noted that the column number of the source matrix A and the target graphic data $B^{(1)}, B^{(2)}, \ldots, B^{(p)}$ is not limited to be t, i.e. the number of periods of the regular check is not limited to be t periods. In other embodiments, the number of the periods of the source matrix A may be less than t, and the number of columns of $B^{(1)}, B^{(2)}, \ldots, B^{(p)}$ is changed to the same as that of the source matrix A.

Moreover, the source graphic data and the best role model graphic data may be now displayed to the user to facilitate the user easily interpreting the health data through a visualized display. Regarding the thermodynamic chart, colors or patterns may be used on the health data to be alerted for user reference so that the data with high complication and low interpretability may be interpreted easily by the user and the user may have a better understanding on the risk of diseases through the comparison with the best role model graphic data.

Figure 4:
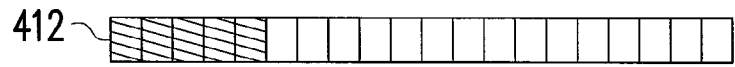
FIG. 4 is an example of source graphic data and best role model graphic data according to an embodiment of the disclosure.
Figure 4:
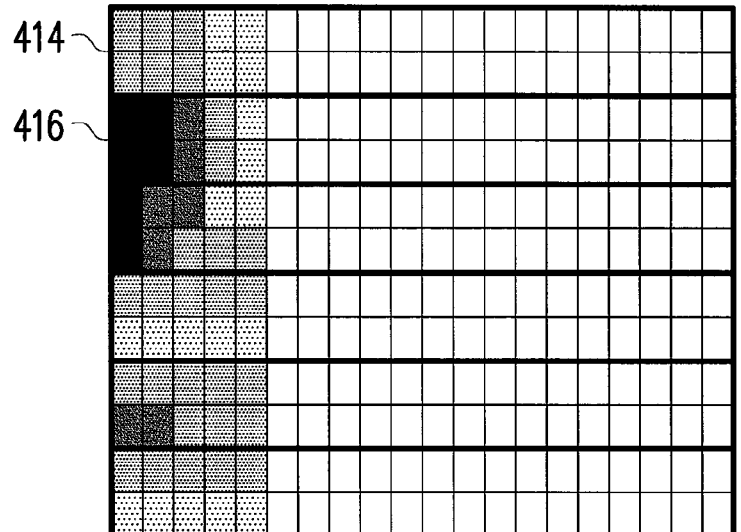
Figure 4:
Figure 4:
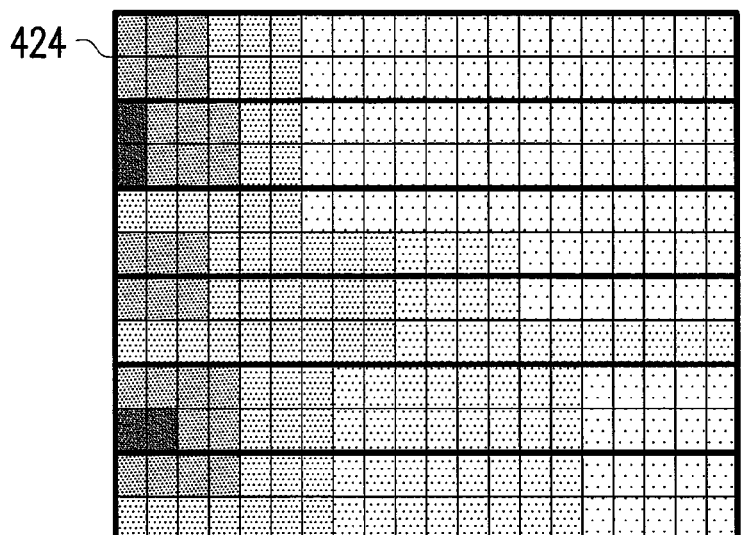
Figure 4:
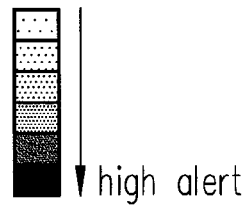

For example, FIG. 4 is an example of the source graphic data and the best role model graphic data according to an embodiment of the disclosure. Referring to FIG. 4, portions with slash lines in a block 412 and a block 422 respectively represent checked periods of source graphic data 410 and best role model graphic data 420. According to the block 412, it is known that the checked periods of the source graphic data 410 is less than the checked periods of the best role model graphic data 420, wherein the source graphic data 410 has 5 checked periods. If the first 5 periods in feature group block 414 of the source graphic data 410 is compared with that in feature group block 424 of the best role model graphic data 420, the graphic data of the compared blocks matches. Namely, the feature group block 424 of the best role model graphic data 420 may be used to predict the health data following the 5 checked periods in the feature group block 414 of the source graphic data 410. Moreover, the health data on high alert in a feature group block 416 of the source graphic data 410 may also be provided in a form of a thermodynamic chart for user reference.

Then, the source graphic data and the best role model graphic data are transmitted to the path development prediction module 180, and the path development prediction module 180 provides a best proposal or an alternative proposal to the user according to the information sample database 170 to facilitate the user selecting one of the proposals (step S206). The information sample database 170 is used to store a plurality of professional medical check proposals, wherein each of the professional medical check proposals includes a plurality of check items and is constructed through continuous field studies. The path development prediction module 180 provides the best proposal according to the best role model graphic data, wherein the check items of the best proposal are completely the same as the check items of the user representing the best role model graphic data. Moreover, the path development prediction module 180 performs path development analysis or risk factor prediction on the health data by using an iterative probability prediction algorithm such as Markov chain, classification of states and transfer matrix, or Metropolis-Hasting sampling through continuous data of the time series as well as selects the alternative proposal from the information sample database 170 to the user, wherein the check items of the alternative proposal are partially the same as the check items of the user representing the best role model graphic data.

Then, the user performs professional medical checks according to the check items of the best proposal or the alternative proposal, and the result of the medical professional checks is fed back to the target graphic database 140 (step S207). Furthermore, if the user selects the check items of the best proposal, after the medical professional checks, if the result thereof matches the disease of the check items, the source graphic data may be stored in the target graphic database 140, wherein the source graphic data becomes newly added target graphic data and the update is completed. If the user selects the check items of the alternative proposal, after the medical professional checks, the result thereof matches the disease of the check items, similarly, the source graphic data may be stored in the target graphic database 140, wherein the source graphic data becomes newly added target graphic data and the update is completed.

Figure 5:
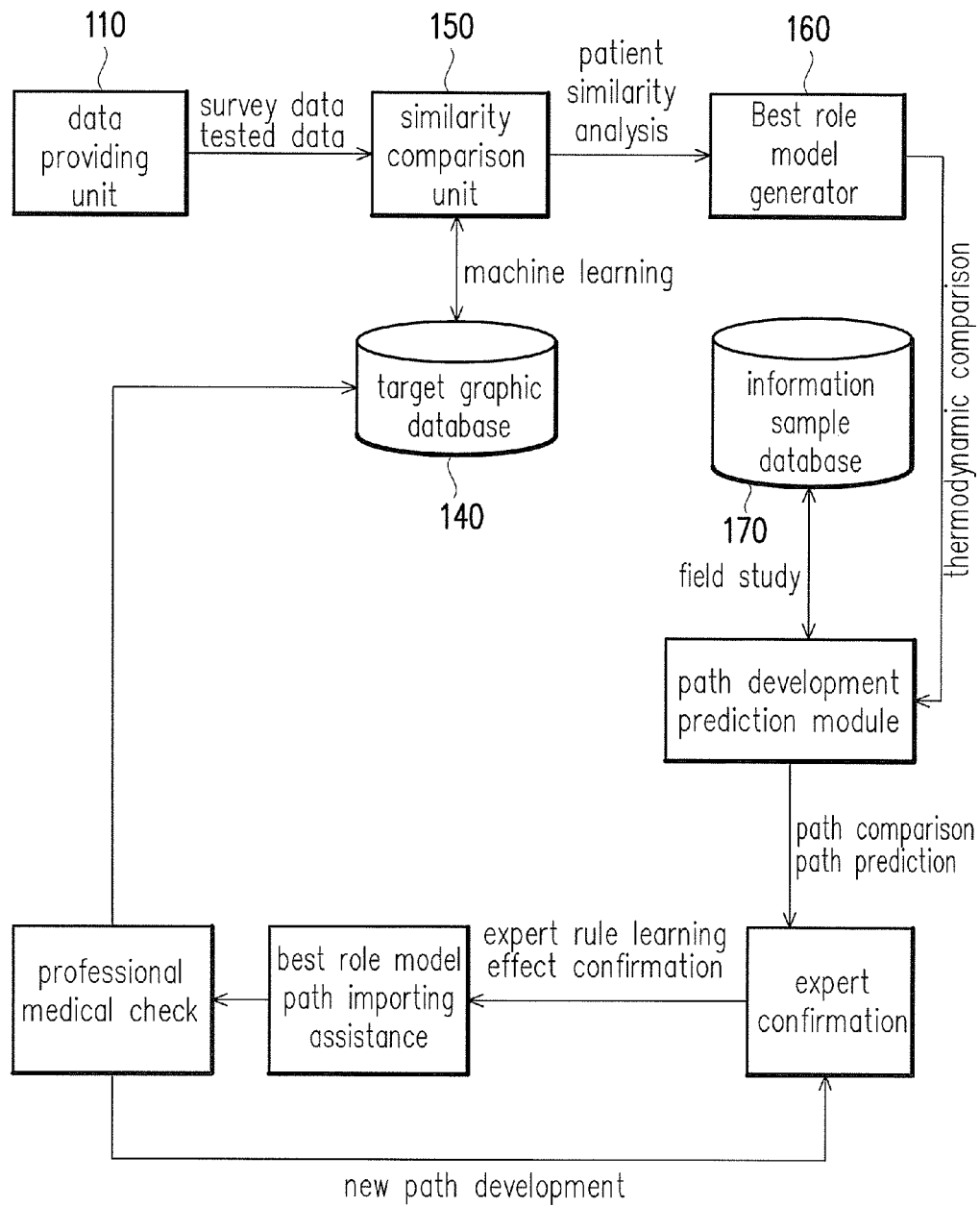
FIG. 5 is a schematic diagram of an operation flow of a health check path evaluation indicator building system according to another embodiment of the disclosure.

In order to fully convey the overall flow of the disclosure, FIG. 5 is a schematic diagram of an operation flow of a health check path evaluation indicator building system according to another embodiment of the disclosure. Referring to FIG. 5, the same components in FIG. 1 and FIG. 5 are denoted by the same reference numbers, and in the present embodiment, the graphic data is presented in form of a thermodynamic chart. First, the data providing unit 110 provides survey data and tested data of the user. Then, the similarity comparison unit 150 performs similarity comparison between the thermodynamic chart of the user and the thermodynamic charts of the other patients stored in the target graphic database 140 so as to perform a similarity analysis by using a machine learning algorithm.

Then, the best role model generator 160 finds the best role model graphic data most similar to the thermodynamic chart of the user. The path development prediction module 180 that uses an iterative probability prediction algorithm such as Markov chain, classification of states and transfer matrix or Metropolis-Hasting sampling performs path development analysis or risk factor prediction according to the information sample database 170 that stores a plurality of professional medical check proposals. After a confirmation is made by experts, one medical professional check proposal is selected for the user. Certainly, the user may also select a medical professional check proposal the same as that of the patient representing the best role model graphic data. No matter if the user selects the medical professional check proposal which is the same as or different to that of the patient representing the best role model graphic data, if the check result matches the disease of the check items, the thermodynamic chart of the user may be stored in the target graphic database 140; if the check result does not match the disease of the check items, further confirmation has to be made by the experts, so as to further discuss whether to perform the other path development analysis or prediction.

In summary, in the health check path evaluation indicator building system and the method thereof, through grouping attributes and using a thermodynamic chart in collaboration with a time series, the health data of the user may be visualized to improve interpretability of the health data. Moreover, the most similar case may be found for the visualized health data through a comparison technique and a method of computer image recognition. The most similar case is set as a reference basis for disease comparison/prediction and professional medical checks so as to take early prevention and treatments for diseases.

In the present disclosure, use of the term "one embodiment" or the similar expression refers to that a specific feature, structure or characteristic described with reference of the concrete embodiment are included in at least one specific embodiment of the disclosure. Therefore, in the disclosure, the term "in a specific embodiment" and the similar expression unnecessarily refer to a same specific embodiment.

Those skilled in the art should understand that the content of the disclosure can be implemented as a computer system, a method thereof or a computer readable medium serving as a computer program product. Therefore, the content of the disclosure can be embodied in various forms such as a complete hardware embodiment or a complete software embodiment (including firmware, resident software and micro-code) which is, for example, executed by a processor or implemented as a software and hardware form. Moreover, the content of the disclosure can also be implemented as a computer program product through any tangible medium form which stores computer executable program codes.

Related description of the content of the disclosure may refer to the flowchart and/or block diagram of the system, device, method and computer program product of the embodiment of the disclosure. Each block in the flowchart and/or block diagram, and any combination of the blocks in the flowchart and/or block diagram can be implemented by computer program instructions. Such computer program instructions can be executed by a processor of a general-purpose computer or a special-purpose computer or a machine composed of other programmable data processing devices, and the instructions are executed by the computer or the other programmable data processing device to implement functions or operations described in the flowchart and/or block diagram.

The computer program instructions can also be stored in a computer readable medium to facilitate indicating the computer or the other programmable data processing device to implement specific functions, and the instructions stored in the computer readable medium constitute a finished product, and the included instructions can be used to implement functions or operations described in the flowchart and/or block diagram.

The computer program instructions can also be loaded into the computer or the other programmable data processing device to execute a system operation step on the computer or the other programmable data processing device, and computer implementation program is generated to implement functions or operations described in the flowchart and/or block diagram when the instructions are executed on the computer or the other programmable data processing device.

FIG. 1 to FIG. 5 are flowcharts and block diagrams of applicable structures, functions and operations of the devices, methods, and computer program products of various embodiment of the disclosure. Therefore, each block in the flowchart or the block diagram may represent a module, a section or a part of program codes, which includes one or a plurality of executable instructions to implement a specified logic function. It should be noticed that in some other embodiments, the functions of the blocks can be implemented according to a sequence not as that shown in the figures. For example, two connected blocks shown in the figure can also be simultaneously executed, or can be executed in a reverse sequence in some cases according to involved functions. Moreover, it should be noticed that the blocks of each block diagram and/or flowchart and the combination of the blocks in the flowchart and/or block diagram can be implemented by a hardware system based on a special purpose, or implemented by a combination of hardware and computer instructions with the special purpose to execute specific functions or operations.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A health check path evaluation indicator building method, adapted to a system having a processor, a memory device, and a display, comprising:
   providing a plurality of attributes in a time series by the processor, wherein each of the attributes has a plurality of features;
   performing a visualization process on the features and the attributes by the processor according to the time series to produce source graphic data, wherein the source graphic data has a group number;
   performing a similarity comparison between the source graphic data and a plurality of target graphic data stored in a target graphic database in the memory device with the same group number by the processor to produce a plurality of similarity scores;
   selecting best role model graphic data from the target graphic data by the processor, wherein a similarity score between the source graphic data and the best role model graphic data is the minimum value among the similarity scores;
   controlling the display to display the source graphic data and the best role model graphic data by the processor;
   selecting one of a best proposal and an alternative proposal from an information sample database in the memory device by the processor according to the best role model graphic data, wherein the best proposal and the alternative proposal respectively have a plurality of check items, and wherein all of the check items of the best proposal correspond to the best role model graphic data, and wherein a part of the check items of the alternative proposal corresponds to the best role model graphic data;
   receiving a result of professional medical checks performed according to the check items of the best proposal or the alternative proposal by the processor; and
   feeding back the result of the professional medical checks to the target graphic database by the processor.

2. The health check path evaluation indicator building method as claimed in claim 1, wherein the source graphic data and the target graphic data are a plurality of thermodynamic charts or a plurality of contour maps.

3. The health check path evaluation indicator building method as claimed in claim 2, wherein when the source graphic data and the target graphic data are the thermodynamic charts, an algorithm for calculating the similarity scores is to obtain a squared Euclidean distance, allocate a different weighting parameter to each of the attributes, and dynamically update the weighting parameters and the target graphic database.

4. The health check path evaluation indicator building method as claimed in claim 2, wherein when the source graphic data and the target graphic data are the contour maps, an algorithm for calculating the similarity scores is to perform a difference comparison on interior areas enclosed by closed curves of contour lines.

5. The health check path evaluation indicator building method as claimed in claim 2, wherein an algorithm for performing the similarity comparison to produce the similarity scores comprises multi-dimensional scaling of principal component analysis, multivariate statistical analysis, or pattern recognition and machine learning.

6. The health check path evaluation indicator building method as claimed in claim 1, wherein a method of selecting the alternative proposal according to the best role model graphic data comprises using one of the following algorithms: Markov chain, classification of states and transfer matrix and Metropolis-Hasting sampling.

7. A non-transitory computer readable medium, storing programs to be loaded into a computer system to embody the method as claimed in claim 1.

8. A health check path evaluation indicator building system comprising:
   a display;
   a memory device, comprising a target graphic database for storing a plurality of target graphic data and an information sample database for storing a plurality of proposals, wherein each of the target graphic data has a group number;
   a processor, coupled to the display and the memory device and configured for:
   providing a plurality of attributes in a time series, wherein each of the attributes has a plurality of features;
   performing a visualization process on the features and the attributes according to the time series to produce source graphic data, wherein the source graphic data has a group number;
   performing a similarity comparison between the source graphic data and the plurality target graphic data with the same group number to produce a plurality of similarity scores;
   selecting best role model graphic data from the plurality of target graphic data, wherein the similarity score between the source graphic data and the best role model graphic data is the minimum value among the similarity scores;

controlling the display to display the source graphic data and the best role model graphic data;

selecting one of a best proposal and an alternative proposal from the information sample database according to the best role model graphic data, wherein the best proposal and the alternative proposal respectively have a plurality of check items, and wherein all of the check items of the best proposal correspond to the best role model graphic data, and wherein a part of the check items of the alternative proposal corresponds to the best role model graphic data;

receiving a result of professional medical checks performed according to the check items of the best proposal or the alternative proposal; and feeding back the result of the professional medical checks to the target graphic database.

9. The health check path evaluation indicator building system as claimed in claim 8, wherein the source graphic data and the target graphic data are a plurality of thermodynamic charts or a plurality of contour maps.

10. The health check path evaluation indicator building system as claimed in claim 9, wherein when the source graphic data and the target graphic data are the thermodynamic charts, an algorithm that the similarity comparison unit calculates the similarity scores is to obtain a squared Euclidean distance, allocate a different weighting parameter to each of the attributes, and dynamically update the weighting parameter and the target graphic database.

11. The health check path evaluation indicator building system as claimed in claim 9, wherein when the source graphic data and the target graphic data are the contour maps, an algorithm that the similarity comparison unit calculates the similarity scores is to perform a difference comparison on interior areas enclosed by closed curves of contour lines.

12. The health check path evaluation indicator building system as claimed in claim 9, wherein an algorithm for performing the similarity comparison to produce the similarity scores comprises multi-dimensional scaling of principal component analysis, multivariate statistical analysis, or pattern recognition and machine learning.

13. The health check path evaluation indicator building system as claimed in claim 8, wherein a method of selecting the alternative proposal according to the best role model graphic data comprises using one of the following algorithms: Markov chain, classification of states and transfer matrix, and Metropolis-Hasting sampling.

* * * * *